(12) United States Patent
Kakuo et al.

(10) Patent No.: US 7,887,851 B2
(45) Date of Patent: Feb. 15, 2011

(54) AROMATASE ACTIVATOR

(75) Inventors: Shingo Kakuo, Haga-gun (JP); Shigeru Moriwaki, Haga-gun (JP); Atsushi Ohuchi, Haga-gun (JP); Hiroshi Kusuoku, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/140,960

(22) Filed: Jun. 1, 2005

(65) Prior Publication Data
US 2006/0127412 A1 Jun. 15, 2006

(30) Foreign Application Priority Data

Jun. 7, 2004 (JP) ............................. 2004-168996
Jun. 7, 2004 (JP) ............................. 2004-169052

(51) Int. Cl.
A01N 65/00 (2009.01)
(52) U.S. Cl. .................................. 424/725
(58) Field of Classification Search ............... 424/725, 424/741, 746, 736, 757, 765, 756, 758, 750, 424/770, 195.18, 76.9, 537, 195.15; 514/775, 514/54, 5
See application file for complete search history.

(56) References Cited

U.S. PATENT DOCUMENTS

| | | | |
|---|---|---|---|
| 5,576,303 A * | 11/1996 | Shibuya et al. | |
| 6,335,457 B1 * | 1/2002 | Seguin et al. | |
| 6,409,996 B1 * | 6/2002 | Plaschke | |
| 6,419,962 B1 * | 7/2002 | Yokoyama et al. | |
| 6,440,446 B1 * | 8/2002 | Yoshizane et al. | |
| 6,440,468 B1 * | 8/2002 | Quintanilla Almagro et al. | |
| 6,552,208 B1 * | 4/2003 | Alander et al. | |
| 6,569,471 B2 * | 5/2003 | Winther et al. | |
| 6,635,758 B2 * | 10/2003 | Pan et al. | |
| 6,716,451 B1 * | 4/2004 | Udell et al. | |
| 2001/0002264 A1 * | 5/2001 | Bok et al. | |
| 2002/0040052 A1 * | 4/2002 | Ito et al. | |
| 2004/0265399 A1 | 12/2004 | Kakuo et al. | |

FOREIGN PATENT DOCUMENTS

| | | | |
|---|---|---|---|
| AO | 1 338 283 A1 | | 8/2003 |
| CN | 1210865 A * | | 3/1999 |
| CN | 1490321 A | | 4/2004 |
| JP | 62270700 A * | | 11/1987 |
| JP | 63022508 A * | | 1/1988 |
| JP | 06048952 A * | | 2/1994 |
| JP | 07053351 A1 * | | 2/1995 |
| JP | 08020525 A * | | 1/1996 |
| JP | 09077639 A * | | 3/1997 |
| JP | 09176030 A * | | 7/1997 |
| JP | 2000072652 A * | | 3/2000 |
| JP | 2000316538 A * | | 11/2000 |
| JP | 2002000288 A * | | 1/2002 |
| JP | 2002326947 A * | | 11/2002 |
| JP | 2002-363086 | | 12/2002 |
| JP | 2003104848 A * | | 4/2003 |
| JP | 2003325125 A1 * | | 11/2003 |
| JP | 2004075543 A * | | 3/2004 |
| JP | 2004149432 A * | | 5/2004 |
| WO | WO 99/47149 | | 9/1999 |
| WO | WO 01/31048 A1 * | | 10/1999 |
| WO | WO 00/13661 | | 3/2000 |
| WO | WO 02/17943 A1 * | | 8/2001 |
| WO | WO 2004/030683 A1 | | 4/2004 |

OTHER PUBLICATIONS

Mabberley, D. J. The Plant-Book (1997), Cambridge University Press, United Kingdom, pp. 8, 9, 54-61, 84-87, 124, 125, 174, 175, 198, 199, 230-233, 258, 259, 296, 297, 312, 313, 326, 327, 352, 353, 362-365, 372, 373, 384, 385, 392, 393, 396-401, 408-411.*
Mabberley, D. J. The Plant-Book (1997), Cambridge University Press, United Kingdom, pp. 430-431, 434, 435, 450, 451, 466, 467, 474-477, 524, 525, 558-561, 620-623, 628, 629, 668-671, 734-737, 766 and 767.*
Kao, Y. et al. Environmental Health Perspectives, vol. 106(2): 85-92. (1998). Molecular basis of the inhibition of human aromatase (estrogen synthetase) by flavone and isoflavone phytoestrogens: A site-directed mutagenesis study.*
http://www.pdrhealth.com/drug_info/nmdrugprofiles/nutsupdrugs/chr_0076.shtml.*
Morton, Julia F. 1987. Grapefruit. p. 152-158. In: Fruits of warm climates. Julia F. Morton, Miami, FL.*
Takahashi et al. International Journal of Fertility & Menopausal Studies. 39(2):69-76, Mar-Apr. 1994 Effect of TJ-68 (shakuyaku-kanzo-to) on polycystic ovarian disease.*
Takahashi, K et al. International Journal of Fertility & Menopausal Studies, Mar.-Apr. 1994; 39(2): 69-76. Effect of TJ-68 (Shakuyaku-Kanzo-To) on polycystic ovarian disease.*
Takeuchi, T et al. American Journal of Chinese Medicine, 1989; 17(1-2): 35-44. Effect of traditional herbal medicine, Shakuyaku-Kanzo-To on total and free serum testosterone levels.*
Takeuchi, T et al. American Journal or Chinese Medicine, 1991; 19(1): 73-8. Effect of paeoniflorin, glycyrrhizin and glycyrrhetic acid on ovarian androgen production.*
Jakab, M et al. Acta Pharmaceutica Hungarica, 1960; 30: 170-9. The composition of the royal jelly of bee (*Apis mellifica*) and its effect on human beings. Abstract.*
ILee, T-K et al. Immunopharmacol Immunotoxicol (Aug. 2004): 26(3): 31-327. Inhibitory effects of Scutellaria Barbata D. Don and Euonymus Alatus Sieb. on aromatase actiivity of leiomyomal cells.*
Lindstedt et al. Acta Chemica Scandinavica (1949), 3, 1375-80. Constituents of pine heartwood. XV. Heartwood of Pinus excelsa.*

(Continued)

Primary Examiner—Michele Flood
(74) Attorney, Agent, or Firm—Oblon, Spivak, McClelland, Maier & Neustadt, L.L.P.

(57) ABSTRACT

Drugs and cosmetics which are highly safe, and which are effective in preventing, improving, or treating various pathological conditions caused by estrogen depletion are provided. Provided are aromatase activators containing at least one member selected from plants such as Labiatae sps. including *Isodon*, *Scutellaria* (huangcen), *Schizonepeta* (jingjie), sage, lavender, *Lamium album*, and thyme, an extract thereof; yeast extract; silk protein extract; milk protein; trehalose; natto extract; royal jelly; *oryza* oil; hydrolyzated wheat extract; shea butter; and rice fermentation extract.

10 Claims, No Drawings

OTHER PUBLICATIONS

Birch, A. J.; Salahuddin, M. Tetrahedron Letters (1964), (31-32), 2211-14. A natural flavan. Abstract.*

Ososkii, A. L. et al. Phytotherapy Research (2003): 17(8): 845-869. Phytoestrogens: a review of the present sate of research.*

Eskai, S. Nippon Yakurigaku Zasshi (1968). 64(2): 186-98. Pharmacological studies on tectoridin and tectorigenin.*

Kawase, A et al. Agricultural and Biological Chemistry (1973), 37(1), 145-50. Flavonoid of iridaceae. II. Chemical structure of a new isoflavone glucoside, homotectoridin, isolated together with tectoridin from the rhizomes. Abstract.*

PTO Jul. 1288; Translation of Nichi Yakur Shi (J of Japanense Pharmacology Assoc), 64: 186-198 (1968), "Pharmacological effects of Tectoridin and Tectorigenin" by Shunji Ezaki, pp. 1-20.* http://www.pfatorg/database/plants.php?Iris+germanica+florentina. "Plants for A Future: Iris germanica florentina—(L.)Dykes."Downloaded from world wide web on Jun. 15, 2010.*

T Nikaido, et al., "Inhibition of Cyclic AMP Phosphodiesterase by Flavonoids", Journal of Medicinal Plant Research, Planta Medica, vol. 46, No. 11, Nov. 1982, pp. 162-166.

Nobuhiro Harada, et al., "Unique regulation of expression of human aromatase in the placenta ", The Journal of Steroid Biochemistry & Molecular Biology, vol. 86, No. 3-5, XP-002342087, Sep. 2003, pp. 327-334.

Nobuhiro Harada, "Aberrant Expression of Aromatase in Breast Cancer Tissues", The Journal of Steroid Biochemistry & Molecular Biology, vol. 61, No. 3-6, XP-002342088, Apr. 1997, pp. 175-184.

Hidetaka Morinaga, et al., "A Benzimidazole Fungicide, Benomyl, and its Metabolite, Carbendazim, Induce Aromatase Activity in a Human Ovarian Granulose-Like Tumor Cell Line (KGN)", Endocrinology, vol. 145, No. 4, XP-002342089, Apr. 2004, pp. 1860-1869.

David T. Zava, et al., "Estrogen and Progestin Bioactivity of Foods, Herbs, and Spices (44247)", Proceedings of the Society for Experimental Biology and Medicine, vol. 217, No. 3, XP-008026916, 1998, pp. 369-378.

Shiuan Chen, et al., "Modulation of aromatase expression in human breast tissue", The Journal of Steroid Biochemistry & Molecular Biology, vol. 79, No. 1-5, XP-002342090, Dec. 2001, pp. 35-40.

Hyeh-Jean Jeong, et al., "Aromatase Inhibitors from Isodon Excisus var. coreanus", Archives of Pharmacal Research, vol. 23, No. 3, XP-008051234, Jun. 2000, pp. 243-245.

Tae-Kyun Lee, et al., "Inhibitory Effects of Scutellaria Barbata D. Don. and Euonymus Alatus Sieb. on Aromatase Activity of Human Leiomyomal Cells", Immunopharmacology and Immunotoxicology, vol. 26, No. 3, XP-008051235, Aug. 2004, pp. 315-327.

Bu-Miin Huang, et al., Upregulation of Steroidogenic Enzymes and Ovarian 17β-Estradiol in Human Granulosa-Lutein Cells by Cordyceps sinensis Mycelium[1], Biology of Reproduction, vol. 70, No. 5, XP-002342091, May 2004, pp. 1358-1364.

Toru Takeuchi, et al., "Effect of Paeoniflorin, Glycyrrhizin and Glycyrrhetic acid on Ovarian Androgen Production", American Journal of Chinese Medicine, vol. XIX, No. 1, XP-008051240, 1991, pp. 73-78.

Hirotaka Ota, et al., "Stimulatory Action of Shakuyaku on Aromatase Activity in Cultured Rat Follicles", Acta Obst Gynaec Jpn, vol. 41, No. 5, XP-008051238, May 1989, pp. 525-529.

Kentaru Takahashi, et al., "Effect of TJ-68 (Shakuyaku-Kanzo-To) on Polycystic Ovarian Disease", International Journal of Fertility and Menopausal Studies, vol. 39, No. 2, XP-008051237, Mar. 1994, pp. 69-76.

Database Biosis 'Online!, AN PREV198375073483, XP-002342115, 1982, 2 pages.

Jean-Christophe Le Bail, et al., "Chalcones are potent inhibitors of aromatase and 17β-hydroxysteroid dehydrogenase activities", Life Sciences, vol. 68, XP-002241304, 2001, pp. 751-761.

Najia Guthrie, et al., "Effectiveness of Citrus Flavonoids on Human Prostate, Colon, Lung, and Melanoma Cancer-Cell Proliferation", American Chemical Society, vol. 219, No. 1/2, XP-008016727, Mar. 26, 2000, p. AFGD183.

E R. Rosenblum et al., "Assessment of the Estrogenic Activity of Phytoestrogens Isolated from Bourbon and Beer", Alcoholism Clinical and Experimental Research, vol. 17, No. 6, Nov./Dec. 1993, pp. 1207-1209.

Kunio Seki, et al., "Studies on Hypolipidemic Agents. IV." Influence of a New Hypolipidemic Agent, 5-Tridecylpyrazole-3-carboxylic Acid, on Cholesterol Metabolism in Rats, Chem. Pharm. Bull., vol. 33, 1985, pp. 5036-5041.

Munehisa Arisawa, et al., "Studies of Constituents of Iris Genus Plants. VI.[1)]The Constituents of the Rhizoma of *Iris florentina* L. and the Constituents of the Petals of *Iris japonica* Thunb.", Yakugaku Zasshi, Pharmaceutical Society of Japan, 93 (12), 1973, pp. 1655-1659 (with English Abstract).

Masayuki Yoshikawa, et al., "Absolute Stereostructures of 3S-Phyllodulcin. 3R- and 3S-Thunberginol H Glycosides From the Leaves of Hydrangea Macrophylla Seringe Var. Thunbergii Makino[1]", Heterocycles, vol. 50, No. 1, 1999, pp. 411-418.

* cited by examiner

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Synthetic DNA

<400> SEQUENCE: 1
gactagtaaa caaccacaaa actgctc          27

<210> SEQ ID NO 2
<211> LENGTH: 28
<212> TYPE: DNA
<213> ORGANISM: Artificial Sequence
<220> FEATURE:
<223> OTHER INFORMATION: Synthetic DNA

<400> SEQUENCE: 2
aactgcagac aagtcaaaac aaggaagc          28

<210> SEQ ID NO 3
<211> LENGTH: 26
<212> TYPE: DNA
<213> ORGANISM: Artificial Sequence
<220> FEATURE:
<223> OTHER INFORMATION: Synthetic DNA

<400> SEQUENCE: 3
gactagtaag gtgcagtgac aggctc          26

<210> SEQ ID NO 4
<211> LENGTH: 27
<212> TYPE: DNA
<213> ORGANISM: Artificial Sequence
<220> FEATURE:
<223> OTHER INFORMATION: Synthetic DNA

```
<400> SEQUENCE: 4
ggaattcctg tcaggctcca gttggtc                                    27
```

AROMATASE ACTIVATOR

FIELD OF THE INVENTION

This invention relates to an aromatase activator for increasing activity of aromatase which is an enzyme involved in biosynthesis of estrogen from androgen.

BACKGROUND OF THE INVENTION

Estrogen which is known to be a female sex hormone is produced in human mainly by ovary, and known types include 17β-estradiol, estrone, and estriol.

Estrogen is involved in various physiological functions including propagation of endometrium, regulation of sexual functions, regulation of bone metabolism, and regulation of lipid metabolism, and therefore, estrogen depletion caused by aging or weakening of ovarian function results in symptoms such as climacteric disturbance, hypogonadism, autonomic imbalance, lipidosis, vasomotor disturbance, and osteoporosis.

In the meanwhile, prevention or improvement of such symptoms by direct administration of estrogen or estrogenic substance would be inappropriate since they have EDC (endocrine disrupting chemical) action.

SUMMARY OF THE INVENTION

This invention provides an aromatase activator containing at least one member selected from the group consisting of Labiatae spp. which are *Isodon*, *Scutellaria* (huangcen), *Schizonepeta* (jingjie), sage, lavender, *Lamium album*, and thyme; Umbelliferae spp. which are fennel (huixiang), cnidium (chuangong), glehnia, angelica (danggui), *bupleurum* (chaihu), *Saposhnikovia* (fang feng), and angelica (baizhi); Rutaceae spp. which are bitter orange (zhishi), *Evodia* (wuzhuyu), zanthoxylum, tangerine (chenpi), bitter orange (toupi), lemon, and grapefruit; Compositae spp. which are lettuce, Roman chamomile, *arnica, Atractylodes* (bai zhu), safflower, and yarrow; Leguminosae spp. which are liquorice (gancao), *Sophora* (kushen), restharrow, tragacanth, and cassia (juemingzi); Rosaceae spp. which are hawthorn (shanzhazi), apple, burnet, and whitethorn; Zingiberaceae spp. which are turmeric (yujin), zedoary (woshu), cardamom, and ginger (shengjiang); Moraceae spp. which are mulberry (sangbaipi) and hop; Liliaceae spp. which are butcher's broom and lily; Gentianaceae spp. which are gentian (longdan) and gentian; Gramineae spp. which are sasa and imperata; Iridaceae sp which is *iris* (*iris* root); Lauraceae sp which is cinnamon; Juglandaceae sp which is *Engelhardtia*; Asclepiadaceae sp which is condurango; an Aristolochiaceae sp which is *asiasarum* (xixin); Dioscoreaceae sp which is *dioscorea* (shanyao); Acoraceae sp which is sweet flag; Betulaceae sp which is birch; Caprifoliaceae sp which is honeysuckle (rendong); Myrtaceae sp which is cloves; Hamamelidaceae sp which is *hamamelis*; Menispermaceae sp which is *Sinomenium* (fangyi); Ephedraceae sp which is *ephedra* herb (mahuang); Ganodermataceae sp which is ling zhi; Hydrangeaceae sp which is sweet hydrangeae; Papaveraceae sp which is *corydalis* (yanhusuo); Bignoniaceae sp which is *catalpa*; Magnoliaceae sp which is *magnolia* (houpu); Malvaceae sp which is mallow; Solanaceae sp which is tomato; Cucurbitaceae sp which is *luffa*; Pinaceae sp which is rosin; and Typhaceae sp. which is reed mace; an extract thereof; yeast extract; silk protein extract; milk protein; trehalose; natto extract; royal jelly; *oryza* oil; hydrolyzated wheat extract; shea butter; and rice fermentation extract.

This invention also provides use of the plant or the extract thereof, yeast extract, silk protein extract, milk protein, trehalose, natto extract, royal jelly, *oryza* oil, hydrolyzed wheat extract, Shea butter, or rice fermentation extract as described above for producing an aromatase activator.

This invention also provides a method for activating aromatase including administering the plant or the extract thereof, yeast extract, silk protein extract, milk protein, trehalose, natto extract, royal jelly, *oryza* oil, hydrolyzed wheat extract, Shea butter, or rice fermentation extract as described above to a human individual.

DETAILED DESCRIPTION OF THE INVENTION

This invention relates to provision of a drug or a cosmetic which is highly safe, and which is effective in preventing, improving, or treating various conditions as described above caused by estrogen depletion through promotion of estrogen production in the body.

The inventors of the present invention focused attention on biosynthesis of androgen from estrogen by aromatase, and investigated natural substances that are capable of enhancing aromatase activity. The inventors then found that particular plants and algae exhibit aromatase activating actions.

The aromatase activator of the present invention is capable of promoting estrogen synthesis in the body, and is also highly safe to human body. Therefore, its use as a drug or a cosmetic for preventing, improving, or treating various pathological conditions caused by estrogen depletion is quite effective.

In the aromatase activator of the present invention, *Isodon* means *Isodon japonicus* or *I. trichocarpus* in the family Labiatae; *Scutellaria* (huangcen) means *Scutellaria baicalensis* in the family Labiatae; *Schizonepeta* (jingjie) means *Schizonepeta tenuifolia* in the family Labiatae; sage means *Salvia officinalis* in the family Labiatae; lavender means *Lavandula angustifolia* in the family Labiatae; *Lamium* means *Lamium album* in the family Labiatae; thyme means *Thymus vulgaris* the family Labiatae; fennel (huixiang) means *Foeniculum vulgare* in the family Umbelliferae; cnidium (chuangong) means *Cnidium officinale* in the family Umbelliferae; glehnia means *Glehnia littoralis* in the family Umbelliferae: angelica (danggui) means *Angelica acutiloba* in the family Umbelliferae; bupleurum (chaihu) means *Bupleurum falcatum* in the family Umbelliferae; *Saposhnikovia* (fang feng) means *Saposhnikovia divaricata* or *Ledebouriella seseloides* in the family Umbelliferae; angelica (baizhi) means *Angelica dahurica* in the family Umbelliferae; bitter orange (zhishi) means *Citrus aurantium* in the family Rutaceae; *Evodia* (wuzhuyu) means *Evodia rutaecarpa* or *C. officinalis* in the family Rutaceae; zanthoxylum means *Zanthoxylum piperitum* in the family Rutaceae; tangerine (chenpi) means *Citrus unshiu* in the family Rutaceae; bitter orange (toupi) means *Citrus aurantium* in the family Rutaceae; lemon means *Citrus limon* in the family Rutaceae; grapefruits means *Citrus paradisi* in the family Rutaceae; lettuce means *Lactuca sativa* in the family Compositae; Roman chamomile means *Anthemis nobilis* in the family Compositae; arnica means *Arnica montana* in the family Compositae; *Atractylodes* (bai zhu) means *Atractylodes japonica* or *A. ovata* in the family Compositae; safflowers means *Carthamus tinctorius* in the family Compositae; yarrow means *Achillea millefolium* in the family Compositae; liquorice (gancao) means *Glycyrrhiza glabra*, *G. uralensis* or *G. inflata* in the family Leguminosae; *Sophora* (kushen) means *Sophora angustifolia* in the family Leguminosae; restharrow means *Ononis spinosa* in the family Leguminosae;

tragacanth means *Astragalus gummifer* in the family Leguminosae; cassia (juemingzi) means *Cassia obtusifolia* in the family Leguminosae; hawthorn (shanzhazi) means *Crataegus cuneata* in the family Rosaceae; apple means *Pyrus malus* in the family Rosaceae; burnet means *Sanguisorba officinalis* in the family Rosaceae; whitethorn means *Crataegus oxyacantha* in the family Rosaceae; turmeric (yujin) means *Curcuma longa* in the family Zingiberaceae; zedoary (woshu) means *Curcuma zedoaria* in the family Zingiberaceae; cardamom means *Elettaria cardamomum* in the family Zingiberaceae; ginger (shengjiang) means *Zingiber officinale* in the family Zingiberaceae; mulberry (sangbaipi) means *Morus alba* or *M. bombycis* in the family Moraceae; hop means *Humulus lupulus* in the family Moraceae; butcher's broom means *Ruscus aculeatus* in the family Liliaceae; lily means *Lilium candidum* in the family Liliaceae; gentian (longdan) means *Gentiana scabra* in the family Gentianaceae; gentian means *Gentiana lutea* in the family Gentianaceae; sasa means *Sasa Veitchii* in the family Gramineae; imperata means *Imperata cylindrica* in the family Gramineae; iris (iris root) means *Iris florentina* in the family Iridaceae; cinnamon means *Cinnamomum cassia* in the family Lauraceae; *Engelhardtia* means *Engelhardtia chrysolepis* in the family Juglandaceae; condurango means *Marsdenia cundurango* in the family Asclepiadaceae; asiasarum (xixin) measn *Asarum sieboldii* or *A. heteropoides* in the family Aristolochiaceae; dioscorea (shanyao) means *Dioscorea japonica* in the family Dioscoreaceae; sweet flag means *Acorus calamus* in the family Acoraceae; birch means *Betula platyphylla* Suk. var. *japonica* in the family Betulaceae; honeysuckle (rendong) means *Lonicera japonica* in the family Caprifoliaceae; cloves means *Syzygium aromaticum* in the family Myrtaceae; hamamelis means *Hamamelis virginiana* in the family Hamamelidaceae; *Sinomenium* (fangyi) means *Sinomenium acutum* in the family Menispermaceae; ephedra herb (mahuang) means *Ephedra sinica* in the family Ephedraceae; ling zhi means *Ganoderma lucidum* in the family Ganodermataceae; sweet hydrangeae means *Hydrangea serrata* in the family Hydrangeaceae; corydalis (yanhusuo) means *Corydalis turtschaninovii* in the family Papaveraceae; catalpa means *Catalpa ovata* in the family Bignoniaceae; magnolia (houpu) means *Magnolia obovata* in the family Magnoliaceae; mallow means *Malva sylvestris* in the family Malvaceae; tomato means *Lycopersicon esculentum* the family Solanaceae; *Luffa* means *Luffa cylindrica* in the family Cucurbitaceae; rosin means *Pinus* spp. in the family Pinaceae; and reed mace means *Typha latifolia* L., *T. orientalis* or *T. augustifolia* in the family Typhaceae.

Yeast extract is an extract produced from a solution obtained by autodigestion or acid-catalyzed hydrolysis of a Saccharomyces yeast, and exemplary commercially available products include the one sold under the product name of "Yeast Liquid B" (Ichimaru Pharcos Co Ltd.). Silk protein extract is an extract obtained by acid-catalyzed hydrolysis of silk protein, and exemplary commercially available products include "Silkgen G Soluble KE" (Ichimaru Pharcos Co Ltd.). Milk proteins include lactose protein, lactoferrin, and the like, and exemplary commercially available products include "Bioderma SX-14" (Ichimaru Pharcos Co Ltd.) and "Lactoferrin S FREE" (Ichimaru Pharcos Co Ltd.). Trehalose is trehalose (molecular formula, $C_{12}H_{22}O_{11}$) and a typical products is "Trehalose" (Hayashibara) Natto extract is an extract produced by extracting natto (fermented soy bean) produced by fermentation of soybeans (*Glycine max*) with *Bacillus subtilis*, and exemplary commercially available products include "Daizu Polymer F B-20" (Ichimaru Pharcos Co Ltd.). Royal jelly is an extract obtained from the substance secreted by European honeybee *Apis mellifica* or Asian honeybee *Apis indica*, and an exemplary commercially available product is "Royal jelly extract" (Ichimaru Pharcos Co Ltd.).

*Oryza* oil is an oil produced from rice bran of rice grains, and an exemplary commercially available product is "*Oryza* oil S-1" (Ichimaru Pharcos Co Ltd.). Shea butter is a fat obtained from shea seeds, and an exemplary commercial available product is "Liquid Shea butter" (Ichimaru Pharcos Co Ltd.). Rice fermentation extract is an extract produced from rice (*Oryza sativa*), and in particular, from the seeds coat of the rice, and an exemplary commercial available product is "rice fermentation extract" (Ichimaru Pharcos Co Ltd.). Hydrolyzed wheat extract is a water-soluble product obtained by hydrolyzing wheat (*Triticum aestivum*) flour, and an exemplary commercial available product is "Gluadin AGP" (Ichimaru Pharcos Co. Ltd.).

The plants as described above may be used either directly or with pulverization, and the part used may be whole plant, leaves, bark, twigs, fruits, roots, or the like. The preferable part used is: above-ground part for *Isodon*; roots for *Scutellaria* (huangcen); above-ground part or spikes for *Schizonepeta* (jingjie); leaves for sage; flowers for lavender; flowers for *Lamium album*; above ground part for thyme; mature fruits for fennel (huixiang); roots for *cnidium* (chuangong); roots and rhizomes for *glehnia*; roots for *angelica* (danggui); roots for *bupleurum* (chaihu); roots for *Saposhnikovia* (fang feng); roots for *angelica* (baizhi); immature fruits for bitter orange (zhishi); fruits for *Evodia* (wuzhuyu); fruits for *zanthoxylum*; pericarp for tangerine (chenpi); pericarp for bitter orange (toupi); fruits for lemon; fruits for grapefruits; leaves for lettuce; flowers for Roman chamomile; flowers for *arnica*; rhizomes for *Atractylodes* (bai zhu); flowers for safflowers; capitula for yarrow; roots for liquorice (gancao); roots for *Sophora* (kushen); roots for restharrow; materials secreted from trunk for tragacanth; seeds for *cassia*; fruits for hawthorn (shanzhazi); fruits for apple; roots for burnet; fruits for whitethorn; rhizomes for turmeric (yujin); rhizomes for zedoary (woshu); fruits for cardamom; rhizomes for ginger (shengjiang); roots bark for mulberry (sangbaipi); Spikes for hop; roots for Butcher's broom; bulbs for lily; roots for gentian (longdan); roots for *gentian*; leaves for *sasa*; rhizomes after removing rootslets and scaly leaves for *imperata*; roots for *iris*; bark for cinnamon; leaves for *Engelhardtia*; bark for *condurango*; roots for *asiasarum* (xixin); rhizomes after removing *dioscorea* (shanyao); roots for sweet flag; bark for birch; flowers for honeysuckle (rendong); flower bud for cloves; leaves for *hamamelis*; stem and rhizomes for *Sinomenium* (fangyi); terrestrial stem for *ephedra* herb (mahuang); fruit bodies for ling zhi; leaves for sweet hydrangeae; tubers for *corydalis* (yanhusuo); pericarp for *catalpa*, bark for *magnolia* (houpu); flowers for *mallow*; fruits for tomato; fruits for *Luffa*; resin remaining after removing essential oil from the secreted material for rosin; and spikes for reed mace.

In the present invention, the term extract includes various extracts obtained by extracting the plant as described above at room temperature or at elevated temperature with or without using an extraction apparatus such as Soxhlet extraction apparatus, a dilution and a concentrate thereof, and a powder produced by drying the extract.

The extraction solvent used extracting the plants of the present invention may be either a polar solvent or a non-polar solvent. Exemplary solvents include water; methanol, ethanol, propanol, butanol and other alcohols; propylene glycol, butylene glycol, and other polyhydric alcohols; acetone, methyl ethyl ketone, and other ketones; methyl acetate, ethyl acetate, and other esters; tetrahydrofurane, diethylether, and other chain or cyclic ethers; polyethyleneglycol and other polyethers; squalane, hexane, cyclohexane, petroleum ether, and other hydrocarbons; toluene and other aromatic hydrocarbons; dichloromethane, chloroform, dichloroethane, and other halogenated hydrocarbons; and carbon dioxide; and mixtures thereof.

The plant extract as described above may be used either with no further processing, or by diluting, concentrating, or freeze drying the extract and preparing a powder or paste.

Also, the plant or the extract thereof may be used after removing inactive contaminants from the extract by an adequate separation techniques such as chromatography.

The plant or the extract thereof, yeast extract, silk protein extract, milk protein, trehalose, natto extract, royal jelly, *oryza* oil, hydrolyzed wheat extract, Shea butter and rice fermentation extract (hereinafter referred to as plants and the like) of the present invention may also be used as a mixture of two or more.

These plants and the like has the action of activating aromatase since they increase expression of the aromatase gene as will be demonstrated in the Examples. Therefore, when the aromatase activator containing the plants and the like incorporated in a drug or a cosmetic is administered to a human individual, estrogen production in the body will be enhanced, and for this, the effects as described below owing to the estrogen are anticipated (Science of Body No. 219, 2001, Nihon Hyron-sha).

(1) Action on bone metabolism: The aromatase activator will suppress function of the parathyroid hormone, thereby suppressing bone resorption, and it will also activate vitamin D in kidney, thereby suppressing the progress of osteoporosis.

(2) Action on hyperlipidemia: The aromatase activator will prevent development of atherosclerosis by the LDL accumulation in blood which is induced by the decrease in the number of LDL receptor due to enhancement of LPL (lipoprotein lipase) activity by the decrease in estrogen concentration. The aromatase activator will also increase expression of mRNA in vascular endothelium to enhance NO production. The aromatase activator will act to facilitate antioxidative action and vasodilating action while it will act to suppress arterial sclerosis.

(3) Action on brain function: The aromatase activator will improve cerebral function such as memory, cognitive function bring change in cerebral blood flow, and influence on feeling and emotion. Relation to depression has also been reported. In the case of Alzheimer's disease, aromatase activator will (i) act on neurons to increase activity of Ach (acetylcholine) synthetase (choline acetyltransferase), (ii) stimulate expression of receptors for nerve growth factor (NGF) and brain-derived neurotrophic factor (BDNF) in cholinergic neuron, (iii) increase number of synapses in hippocampus, (iv) ameliorate neuron damage by reducing the accumulation of β-amyloid by acting on amyloid precursor protein (APP), and (v) improve sugar transportation and utilization in brain.

(4) Action on climacteric disturbance: The aromatase activator will improve autonomic imbalance caused by hyperfunction of hypothalamus and hypophysis due to dysfunctioning of the negative feedback in hypothalamo-hypophysial-ovarian system caused by decrease of estrogen, that is, the autonomic imbalance caused by the increase of LH (luteinizing hormone) and FSH (follicle stimulating hormone).

(5) Action on eye: The aromatase activator will suppress onset of macular degeneration and cataracta which are popular in women after climacterium. It also improves function of lacrimal gland, suppressing dry eye.

When the aromatase activator of the present invention is incorporated in a drug, the drug may take the form of tablet, capsule or other oral medicine, ointment, solution, extract, lotion, emulsion or other external medicine, or injection.

When the aromatase activator of the present invention is incorporated in a cosmetic, the cosmetic may take various forms, for example, water-in-oil or oil-in-water emulsion, cream, lotion, gel, foam, essence, foundation, pack, stick, and powder. The cosmetic may also contain an oil, surfactant, UV absorber, alcohol, chelating agent, pH adjusting agent, antiseptic, thickener, colorant, perfume, skin nutrient, or other components commonly used as a component in the cosmetics in addition to the plant or its extract of the present invention.

Preferably, the plant and the like may be incorporated in the drug or the cosmetic as described above at a content in dry basis of 0.00001 to 1% by weight, preferably at 0.0001 to 0.1% by weight based on the total weight.

EXAMPLES

Next, the present invention is described in further detail by referring to the following Examples.

Production Examples

Preparation of Plant Extracts

Plant extracts as shown in Tables 1 and 2, below were prepared by the ordinary method commonly used in the art.

TABLE 1

| Name of the Extract | Part used | Extraction solvent | Residual content after evaporation |
|---|---|---|---|
| Sweet hydrangeae | Leaves | 50% EtOH | 2.6 w/v % |
| *Arnica* | Flowers | 50% EtOH | 0.9 w/v % |
| Fennel (huixiang) | Mature fruits | 50% EtOH | 4.5 w/v % |
| Turmeric (yujin) | Rhizomes | 50% EtOH | 0.9 w/v % |
| *Corydalis* (yanhusuo) | Tubers | 50% EtOH | 4.0 w/v % |
| Isodon | Above ground part | 50% EtOH | 1.0 w/v % |
| *Scutellaria* (huangcen) | Roots | 50% EtOH | 3.4 w/v % |
| Zedoary (woshu) | Rhizomes | 50% EtOH | 1.7 w/v % |
| *Catalpa* | Pericarp | 50% EtOH | 4.1 w/v % |
| Bitter orange (zhishi) | Immature fruits | 50% EtOH | 14.4 w/v % |
| *Sasa* | Leaves | 50% EtOH | 0.8 w/v % |
| *Schizonepeta* (jingjie) | Above ground part or spikes | 50% EtOH | 1.7 w/v % |
| *Cassia* (juemingzi) | Seed | 50% EtOH | 1.0 w/v % |
| *Magnolia* (houpu) | Bark | 50% EtOH | 4.1 w/v % |
| *Evodia* (wuzhuyu) | Fruits | 50% EtOH | 11.6 w/v % |
| *Bupleurum* (chaihu) | Roots | 50% EtOH | 3.4 w/v % |
| *Asiasarum* (xixin) | Roots | 50% EtOH | 1.3 w/v % |
| *Zanthoxylum* | Fruits | 50% EtOH | 1.5 w/v % |
| Cardamom | Fruits | 50% EtOH | 2.5 w/v % |
| Mallow | Flowers | 50% EtOH | 0.5 w/v % |
| *Cnidium* (chuangong) | Roots | 50% EtOH | 3.6 w/v % |
| *Angelica* (danggui) | Roots | 50% EtOH | 4.2 w/v % |
| Tomato | Fruits | water | 1.0 w/v % |
| *Glehnia* | Roots and rhizomes | 50% EtOH | 9.6 w/v % |
| *Atractylodes* (baizhu) | Rhizomes | 50% EtOH | 8.0 w/v % |
| *Luffa* | Fruits | 50% EtOH | 0.4 w/v % |
| Safflower | Flowers | 95% EtOH | 0.8 w/v % |
| Reed mace | Spikes | 50% EtOH | 1.5 w/v % |
| Lily | Bulbs | 50% EtOH | 0.7 w/v % |
| Gentian (longdan) | Roots | 50% EtOH | 13.1 w/v % |
| Rosin | Resin after removal of essential oil from the secreted material | 50% EtOH | 2.9 w/v % |

TABLE 2

| Name of the extract | Part used | Extraction solvent | Residual content after evaporation |
|---|---|---|---|
| *Iris* (iris root) | Roots | 50% EtOH | 1.3 w/v % |
| *Lamium album* | Flowers | 50% EtOH | 0.2 w/v % |
| Restharrow | Roots | 50% EtOH | 0.8 w/v % |
| Reed mace | Spikes | 50% EtOH | 1.5 w/v % |
| Liquorice (gancao) | Roots | Water | 2.4 w/v % |
| *Sophora* (kushen) | Roots | 50% EtOH | 1.9 w/v % |
| Grapefruits | Fruits | 50% EtOH | 0.6 w/v % |
| Cinnamon | Bark | 50% EtOH | 0.8 w/v % |
| Gentian | Roots | 50% EtOH | 4.2 w/v % |
| *Condurango* | Bark | 50% EtOH | 5.1 w/v % |
| *Asiasarum* (xixin) | Roots | 50% EtOH | 1.3 w/v % |
| Sage | Leaves | 50% EtOH | 2.4 w/v % |
| Hawthorn (shanzhazi) | Fruits | 50% EtOH | 1.2 w/v % |
| *Dioscorea* (shanyao) | Rhizomes after removing periderm | 50% EtOH | 2.4 w/v % |
| Ginger (shengjiang) | Rhizomes | EtOH | 0.5 w/v % |
| Sweet flag | Roots | 50% EtOH | 1.3 w/v % |
| Birch | Bark | 50% EtOH | 1.4 w/v % |
| Honeysuckle (rendong) | Flowers | 50% EtOH | 0.6 w/v % |
| Whitethorn | Fruits | 50% EtOH | 1.3 w/v % |
| Yarrow | Capitula | 50% EtOH | 0.4 w/v % |
| Mulberry (sangbaipi) | Roots bark | 50% EtOH | 1.4 w/v % |
| Thyme | Above-ground part | 50% EtOH | 2.7 w/v % |
| Cloves | Flower buds | 50% EtOH | 2.2 w/v % |
| Tangerine (chenpi) | Pericarp | 50% EtOH | 3.4 w/v % |
| Bitter orange (toupi) | Pericarp | 50% EtOH | 3.7 w/v % |
| Tragacanth | Materials secreted from trunk | 50% EtOH | 7.4 w/v % |
| *Hamamelis* | Leaves | 50% EtOH | 0.2 w/v % |
| *Angelica* (baizhi) | Roots | 50% EtOH | 11.6 w/v % |
| Butcher's broom | Roots | 50% EtOH | 1.2 w/v % |
| *Sinomenium* (fangyi) | Stems and rhizomes | 50% EtOH | 3.3 w/v % |
| *Imperata* | Rhizomes after removing rootslets and scaly leaves | 50% EtOH | 14.2 w/v % |
| *Saposhnikovia* (fang feng) | Roots | 50% EtOH | 5.3 w/v % |
| Hop | Spikes | Water | 2.1 w/v % |
| *Ephedra* herb (mahuang) | Terrestrial stem | 50% EtOH | 5.9 w/v % |
| Lavender | Flowers | 50% EtOH | 2.1 w/v % |
| Apple | Fruits | 50% EtOH | 8.0 w/v % |
| Ling zhi | Fruit bodies | 50% EtOH | 0.4 w/v % |
| Lettuce | Leaves | 50% EtOH | 0.3 w/v % |
| Lemon | Fruits | 50% EtOH | 0.6 w/v % |
| Roman chamomile | Flowers | 50% EtOH | 2.7 w/v % |
| Burnet | Roots | 50% EtOH | 2.2 w/v % |

Referential Example 1

Construction of Reporter Gene Assay System

The region containing transcription control region for exon 1c of human aromatase gene and a part of the exon 1c was amplified by PCR from genomic DNA extracted from human normal keratinocyte by using the following primers:

```
Upper primer,
5'-GACTAGTAAACAACCACAAAACTGCTC-3'   (SEQ ID NO: 1)
Lower primer,
5'-AACTGCAGACAAGTCAAAACAAGGAAGC-3'  (SEQ ID NO: 2)
```

The resulting PCR product was treated with restriction enzymes SpeI and PstI, and incorporated in SpeI site and PstI site in SeaPansy null Control Vector (Toyo Ink Mfg. Co., Ltd.) to produce Ex1c-luc plasmid. This plasmid was used in the luciferase assay as will be described below.

Example 1

Increase in the Expression of Exon 1c of Aromatase Gene (1) Materials and Methods (i) Cells Used
Immortalized keratinocyte-derived cell (HaCaT cell)
(ii) Plasmid Used
About 1 kb of transcription control region for exon 1c of the aromatase gene was incorporated in the upstream of luciferase gene (Ex1c-luc).
(iii) Transfection into the Cell
HaCaT cell was propagated in a 100 mm dish to subconfluency, and Ex1c-luc was introduced using lipofectamine reagent (Invitrogen) according to the protocol described in the attached manual. The DNA was used at an amount of 8 μg per dish. The same procedure was repeated for the control without adding the DNA (1 dish).
(iv) Luciferase Assay
The transfected cells were cultivated overnight, and inoculated to 96 well cell culture plate at about 30,000 cells per well. Total amount of the culture medium was adjusted to be 200 μL. On the next day, plant extract prepared in Production Example 1, Table 1, or oryza oil ("oryza oil S-1", Ichimaru Pharcos Co Ltd.), Shea butter ("Liquid shea butter", Ichimaru Pharcos Co Ltd.), yeast extract ("YeastLiquid B", Ichimaru Pharcos Co Ltd.), rice fermentation extract ("rice fermentation extract", Ichimaru Pharcos Co Ltd.), or hydrolyzed wheat extract ("Gluadin AGP", Ichimaru Pharcos Co Ltd.) was added (1% or 0.1%), and the cultivation was continued for another 20 hours. After adding 20 μL of alamarBlue (BIOSOURCE), fluorescence intensity (excitation light 544 nm, fluorescence 590 nm) was measured. Luciferase activity was also measured by using PicaGene Dual SeaPansy Luminescence kit (Nippon Gene). The cells were lysed by adding 25 μL per well of the lysis buffer that had been diluted 5× lysis buffer to 1× concentration.

(2) Results

The results are shown in Table 3, below.

TABLE 3

| | | Luciferase activity | AlamarBlue activity |
|---|---|---|---|
| Sweet hydrangeae | 1% | 151.8% | 89.1% |
| *Arnica* | 1% | 121.3% | 89.6% |
| Fennel (huixiang) | 0.1% | 135.7% | 103.6% |
| Fennel (huixiang) | 1% | 144.2% | 110.0% |
| Turmeric (yujin) | 1% | 402.2% | 116.2% |
| *Corydalis* (yanhusuo) | 0.1% | 129.8% | 90.0% |

TABLE 3-continued

|  |  | Luciferase activity | AlamarBlue activity |
|---|---|---|---|
| Corydalis (yanhusuo) | 1% | 135.3% | 76.6% |
| Isodon | 1% | 144.0% | 113.9% |
| Scutellaria (huangcen) | 1% | 163.6% | 62.8% |
| Scutellaria (huangcen) | 0.1% | 139.2% | 91.4% |
| Phellodendron | 1% | 136.2% | 92.6% |
| Oryza oil | 0.1% | 142.5% | 85.5% |
| Oryza oil | 1% | 134.0% | 98.2% |
| zedoary (woshu) | 0.1% | 125.4% | 74.4% |
| Catalpa | 1% | 142.2% | 97.4% |
| Bitter orange (zhishi) | 0.1% | 135.5% | 66.2% |
| Bitter orange (zhishi) | 1% | 124.5% | 64.8% |
| Sasa | 0.1% | 128.8% | 99.9% |
| Hydrolyzed wheat extract | 0.1% | 121.3% | 102.0% |
| Schizonepeta (jingjie) | 0.1% | 125.1% | 117.6% |
| Schizonepeta (jingjie) | 1% | 177.5% | 121.9% |
| Cassia (juemingzi) | 1% | 127.1% | 100.0% |
| Magnolia (houpu) | 0.1% | 214.0% | 100.0% |
| Evodia (wuzhuyu) | 0.1% | 140.2% | 104.2% |
| Bupleurum (chaihu) | 1% | 139.5% | 96.2% |
| Asiasarum (xixin) | 1% | 134.7% | 94.1% |
| Zanthoxylum | 1% | 162.4% | 97.2% |
| Cardamom | 1% | 162.4% | 126.4% |
| Mallow | 1% | 182.2% | 93.6% |
| Cnidium (chuangong) | 0.1% | 133.3% | 99.8% |
| Cnidium (chuangong) | 1% | 172.5% | 99.1% |
| Angelica (danggui) | 0.1% | 122.0% | 85.1% |
| Angelica (danggui) | 1% | 175.1% | 87.9% |
| Tomato | 0.1% | 127.2% | 84.0% |
| Tomato | 1% | 151.3% | 79.9% |
| Glehnia | 1% | 121.4% | 190.1% |
| Atractylodes (bai zhu) | 1% | 123.2% | 128.4% |
| Luffa | 0.1% | 123.9% | 90.8% |
| Luffa | 1% | 138.2% | 89.2% |
| Safflower | 0.1% | 122.5% | 104.8% |
| Safflower | 1% | 160.8% | 133.8% |
| Reed mace | 1% | 122.2% | 87.9% |
| Lily | 1% | 122.3% | 121.9% |
| Gentian (longdan) | 1% | 134.0% | 159.4% |
| Rosin | 1% | 140.2% | 111.6% |
| Shea butter | 0.1% | 125.5% | 95.9% |
| Shea butter | 1% | 133.8% | 104.1% |
| Rice fermentation extract | 1% | 134.7% | 98.1% |

The results indicate that the extracts tested are capable of activating aromatase expression.

Referential Example 2

Construction of Reporter Gene Assay System

The region containing transcription control region for exon 1b of human aromatase gene and a part of the exon 1b was amplified by PCR from genomic DNA extracted from human normal keratinocyte by using the following primers:

```
Upper primer,
5'-GACTAGTAAGGTGCAGTGACAGGCTC-3'    (SEQ ID NO: 3)

Lower primer,
5'-GGAATTCCTGTCAGGCTCCAGTTGGTC-3'   (SEQ ID NO: 4)
```

The resulting PCR product was treated with restriction enzymes SpeI and EcoRI, and incorporated in SpeI site and EcoRI site in SeaPansy null Control Vector (Toyo Ink Mfg. Co., Ltd.) to produce Ex1b-luc plasmid. This plasmid was used in the luciferase assay as will be described below.

Example 2

Increase in the Expression of Exon 1b of Aromatase Gene (1) Materials and Methods (i) Cells Used
Immortalized human hepatoma-derived cell (HepG2 cell)
(ii) Plasmid Used
About 1 kb of transcription control region for exon 1b of the aromatase gene was incorporated in the upstream of luciferase gene (Ex1b-luc).
(iii) Transfection into the Cell
HepG2 cell was inoculated to 96 well culture plate at 30,000 cells per well, and Ex1b-luc was introduced using lipofectamine reagent (Invitrogen) according to the protocol described in the attached manual. The DNA was used at an amount of 0.1 μg per well. The same procedure was repeated for control without adding the DNA (2 wells).
(iv) Luciferase Assay
The transfected cells were cultivated overnight, and plant extract prepared in Production Example 1, Table 2, or yeast extract ("YeastLiquid B", Ichimaru Pharcos Co Ltd.), silk protein extract ("Silkgen G Soluble KE", Ichimaru Pharcos Co Ltd.), milk protein ("Bioderma SX-14" Ichimaru Pharcos Co Ltd.), "lactoferrin S FREE", Ichimaru Pharcos Co Ltd.), natto extract ("Soybean polymer F B-20", Ichimaru Pharcos Co Ltd.), or royal jelly ("royal jelly extract", Ichimaru Pharcos Co Ltd.) was added (1% or 0.1%), and the cultivation was continued for another 20 hours. After adding 20 μL of alamarBlue (BIOSOURCE), fluorescence intensity (excitation light 544 nm, fluorescence 590 nm) was measured. Luciferase activity was also measured by using PicaGene Dual SeaPansy Luminescence kit (Nippon Gene). The cells were lysed by adding 25 μL per well of the lysis buffer that had been diluted 5× lysis buffer to 1× concentration.

(2) Results

The results are shown in Table 4, below.

TABLE 4

|  |  | Luciferase activity | AlamarBlue activity |
|---|---|---|---|
| Iris (iris root) | 0.1% | 133.3% | 120.2% |
| Iris (iris root) | 1% | 202.5% | 123.3% |
| Lamium album | 1% | 123.2% | 91.5% |
| Restharrow | 0.1% | 121.5% | 102.5% |
| Restharrow | 1% | 139.0% | 103.4% |
| Reed mace | 1% | 130.1% | 124.3% |
| Liquorice (gancao) | 0.1% | 122.0% | 102.5% |
| Silk protein extract | 0.1% | 173.9% | 170.3% |
| Silk protein extract | 1% | 122.1% | 124.0% |
| Lactose protein | 0.1% | 135.4% | 109.1% |
| Lactose protein | 1% | 133.5% | 129.0% |
| Lactoferrin | 0.1% | 155.2% | 135.9% |
| Lactoferrin | 1% | 181.5% | 138.2% |
| Sophora (kushen) | 0.1% | 142.9% | 160.1% |
| Grapefruit | 0.1% | 120.7% | 140.1% |
| Grapefruit | 1% | 125.9% | 132.7% |
| Cinnamon | 0.1% | 121.7% | 81.8% |
| Gentian | 0.1% | 131.1% | 123.9% |
| Gentian | 1% | 122.4% | 120.4% |
| Engelhardtia | 0.1% | 130.5% | 118.7% |
| Engelhardtia | 1% | 156.9% | 127.6% |

TABLE 4-continued

| | | Luciferase activity | AlamarBlue activity |
|---|---|---|---|
| Yeast extract | 1% | 133.6% | 83.4% |
| *Condurango* | 0.1% | 147.7% | 107.2% |
| *Asiasarum* (xixin) | 0.1% | 130.7% | 122.1% |
| *Asiasarum* (xixin) | 1% | 134.0% | 118.9% |
| Sage | 0.1% | 141.1% | 92.7% |
| Hawthorn (shanzhazi) | 1% | 144.3% | 100.1% |
| *Dioscorea* (shanyao) | 0.1% | 121.4% | 85.2% |
| Ginger (shengjiang) | 0.1% | 123.1% | 115.9% |
| Sweet flag | 1% | 149.6% | 73.6% |
| Birch | 1% | 139.8% | 70.3% |
| Honeysuckle (rendong) | 0.1% | 125.2% | 84.1% |
| Honeysuckle (rendong) | 1% | 135.1% | 77.9% |
| Whitethorn | 0.1% | 137.1% | 84.9% |
| Whitethorn | 1% | 152.9% | 77.1% |
| Yarrow | 1% | 149.3% | 67.9% |
| Mulberry (sangbaipi) | 1% | 137.8% | 90.1% |
| Natto extract | 0.1% | 150.0% | 108.0% |
| Thyme | 1% | 135.5% | 109.7% |
| Cloves | 1% | 175.2% | 76.5% |
| Tangerine (chenpi) | 0.1% | 131.5% | 112.2% |
| Trehalose | 1% | 141.0% | 113.9% |
| Bitter orange (toupi) | 1% | 157.9% | 119.5% |
| Tragacanth | 1% | 121.5% | 94.5% |
| *Hamamelis* | 1% | 129.9% | 126.0% |
| *Angelica* (baizhi) | 0.1% | 247.7% | 97.2% |
| Butcher's broom | 0.1% | 132.8% | 118.1% |
| *Sinomenium* (fangyi) | 0.1% | 129.5% | 91.0% |
| *Sinomenium* (fangyi) | 1% | 150.8% | 82.9% |
| *Imperata* | 0.1% | 123.6% | 90.9% |
| *Saposhnikovia* (fang feng) | 0.1% | 139.1% | 106.6% |
| Hop | 0.1% | 128.4% | 102.2% |
| Hop | 1% | 123.4% | 109.2% |
| *Ephedra* herb (mahuang) | 0.1% | 124.6% | 87.8% |
| Lavender | 1% | 123.0% | 95.1% |
| Apple | 1% | 140.6% | 100.5% |
| Ling zhi | 1% | 166.0% | 154.6% |
| Lettuce | 1% | 149.6% | 133.9% |
| Lemon | 1% | 146.1% | 90.9% |
| Roman chamomile | 0.1% | 137.5% | 178.4% |
| Roman chamomile | 1% | 171.2% | 175.1% |
| Royal jelly | 0.1% | 120.1% | 142.5% |
| Burnet | 0.1% | 130.0% | 83.0% |

The results indicate that the extracts tested are capable of activating aromatase expression.

---

The invention claimed is:

1. A method of increasing expression of the aromatase gene comprising treating a cell population with an effective amount of an aromatase activator comprising an ethanol extract of *Iris florentina*, wherein said effective amount ranges from 0.0001 to 1% by weight based on the total weight of the aromatase activator on a dry basis.

2. The method of claim 1, wherein the treating comprises administering the aromatase activator to a human.

3. The method of claim 2, wherein the aromatase activator is in a form of a cosmetic.

4. The method of claim 2, wherein the aromatase activator is in a form of a drug.

5. The method of claim 2, wherein the aromatase activator is administered orally, is injected, or is topically administered.

6. The method of claim 1, wherein the ethanol extract of *Iris florentina* is an ethanol extract of roots of *Iris florentina*.

7. The method of claim 6 wherein the treating comprises administering the aromatase activator to a human.

8. The method of claim 7, wherein the aromatase activator is in a form of a cosmetic.

9. The method of claim 7, wherein the aromatase activator is in a form of a drug.

10. The method of claim 7, wherein the aromatase activator is administered orally, is injected, or is topically administered.

* * * * *